(12) United States Patent
Lee et al.

(10) Patent No.: US 7,528,285 B2
(45) Date of Patent: May 5, 2009

(54) METHOD FOR PREPARING THIOMETHYLPHENOLS

(75) Inventors: Hyung-Jae Lee, Daejeon (KR); Jin-Eok Kim, Daejeon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 10 days.

(21) Appl. No.: 11/746,833

(22) Filed: May 10, 2007

(65) Prior Publication Data

US 2008/0081929 A1 Apr. 3, 2008

(30) Foreign Application Priority Data

Sep. 29, 2006 (KR) ............ 10-2006-0096110
Sep. 29, 2006 (KR) ............ 10-2006-0096111

(51) Int. Cl.
*C07C 331/00* (2006.01)
(52) U.S. Cl. ............ 568/75; 568/52; 568/51; 568/58
(58) Field of Classification Search ............ 568/75, 568/51, 52, 58
See application file for complete search history.

(56) References Cited

U.S. PATENT DOCUMENTS

| 4,091,037 | A | | 5/1978 | Arold | |
|---|---|---|---|---|---|
| 4,304,940 | A | * | 12/1981 | Wedemeyer et al. | 568/45 |
| 4,874,885 | A | * | 10/1989 | Stegmann et al. | 560/15 |
| 6,365,781 | B2 | * | 4/2002 | Pizzoli et al. | 568/52 |

FOREIGN PATENT DOCUMENTS

| CN | 1515549 | * | 7/2004 |
|---|---|---|---|
| KR | 2001-0000988 | | 8/1995 |
| KR | 1995-9748 A | | 7/2001 |

* cited by examiner

*Primary Examiner*—Daniel M Sullivan
*Assistant Examiner*—Chukwuma O Nwaonicha
(74) *Attorney, Agent, or Firm*—Martin Fleit; Paul Bianco; Fleit Gibbons Gutman Bongini & Bianco PL

(57) ABSTRACT

The present invention relates to a process for preparing thiomethylphenol derivatives, and particularly to a simple process of preparing thiophenol derivatives by performing a reaction of a phenol derivative, a mercaptan derivative and paraformaldehyde in a solvent in the presence of a given amount of heterocyclic amine base and acids, thereby capable of maintaining a mild reaction condition and providing thiomethylphenol derivatives with an improved discoloration by purification using acids.

16 Claims, No Drawings

METHOD FOR PREPARING THIOMETHYLPHENOLS

CROSS-REFERENCE TO RELATED APPLICATIONS

This application claims the benefit of Korean Patent Application No.'s 10-2006-0096110, filed on Sep. 29, 2006, and 10-2006-0096111, filed Sep. 29, 2006, the entire disclosure of each of which is hereby incorporated by reference.

BACKGROUND OF THE INVENTION

Thiomethylphenols are widely used as an important antioxidant in plastics, elastomers, mineral oils and synthetic oils.

With regard to a process for manufacturing the thiomethylphenol derivatives, U.S. Pat. No. 4,091,037 discloses a process comprising the step of reacting 2-(dimethylaminomethyl)-4-methylphenol with thioacetic acid. U.S. Pat. No. 4,304,940 discloses a process comprising the step of reacting phenol with paraformaldehyde and mercaptan derivatives in the presence of Zn(OAc)2. Korean patent publication No. 1995-9748 and U.S. Pat. No. 4,874,885 disclose a process for preparing a yellow liquid of thiomethylphenol derivatives, which comprises the step of reacting formaldehyde and mercaptan derivative in a solvent such as N,N-dimethylformamide at 155° C. for 2 hours in the presence of a base such as mono-, di-, or trimethylamine or mono- or diethylamine.

Besides, Korean patent application No. 2001-0000988 and U.S. Pat. No. 6,365,781 disclose a process for preparing thiomethylphenol derivatives, which comprises the step of reacting formaldehyde and mercaptan derivatives in the presence of mono, di, or trimethylamine or mono or diethylamine base without using a solvent at 130° C. for 3.5 hours, and treating the products with a reducing agent at 90° C. for 7 hours. In theses patents, the base is limited to mono dimethylamine, dimethylamine, monoethylamine and diethylamine.

However, the aforementioned processes have drawbacks that they require a high reaction temperature, a long period of time for either the reaction or the purification, and a discoloration resulted from the oxidation of a base.

Therefore, an object of the present invention is to provide a process for preparing colorless thiomethylphenol derivatives, which may increase the reaction rate and improve discoloration even at a relatively mild condition.

DETAILED DESCRIPTION OF THE INVENTION

The present inventors have performed extensive studies and made efforts to solve the aforementioned problems, i.e. harsh reaction conditions, discoloration of thiomethylphenol derivatives during both the reaction and the purification and the resulting deterioration of the products. As a result, the present inventors have finally discovered that a process for preparing thiomethylphenol derivatives, which comprises the step of reacting a phenol derivative, a mercaptan derivative and paraformaldehyde in a solvent in the presence of a heterocyclic amine base and an acid has the advantages as follows: (i) the acid inhibits the discoloration of the resulting product, (ii) the solvent increases the reaction rate, and (iii) the aminomethanol, i.e. an intermediate product produced from the base and the paraformaldehyde, is converted into a highly reactive imine by the acid, thereby maximizing the reactivity with a phenol and keeping the reaction condition milder than that of the reaction between an aminomethanol and a phenol.

The present invention has been completed based on the aforementioned findings along with the following finding that the purification of thus obtained thiomethylphenol derivatives by addition of a given amount of acid may decompose or remove the aminomethanol, i.e. an intermediate product, through the neutralization, thus enabling to improve the discoloration and finally manufacture colorless thiomethylphenol derivatives.

The present invention relates to a process of preparing thiomethylphenol derivatives, and particularly to a simple process of preparing thiomethylphenol derivatives by performing a reaction of a phenol derivative, a mercaptan derivative and a paraformaldehyde in a solvent in the presence of a given amount of heterocyclic amine base and acids, thereby capable of maintaining a mild reaction condition and providing thiomethylphenol derivatives with an improved discoloration through a purification step using acids.

The present invention relates to a process of preparing a thiomethylphenol derivative of Formula (I) by performing a reaction of a phenol derivative of Formula (II), a mercaptan derivative of $R^2SH$ and paraformaldehyde in a solvent in the presence of a $C_4$-$C_{10}$ heterocyclic amine base and an acid:

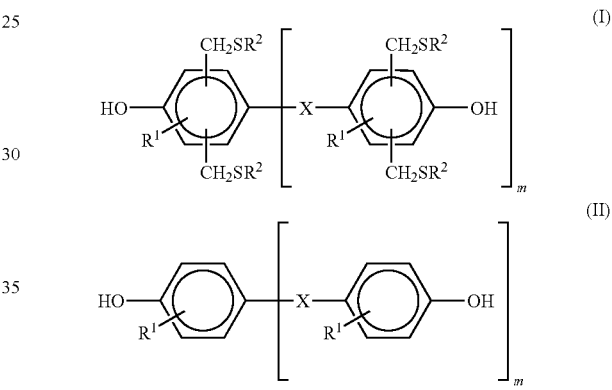

wherein $R^1$ is a hydrogen atom, a $C_1$-$C_{16}$ linear or branched alkyl, or an alkyl group comprising an aromatic group; $R^2$ is a $C_1$-$C_{16}$ linear or branched alkyl or an alkyl group comprising an aromatic group; X is a hydrogen atom, —$(CH_2)_n$—, —$CMe_2$— or —Y— wherein Y is an aromatic compound such as benzene, biphenyl, toluene and naphthalene or an aromatic compound having at least one substituted alkyl group; n is an integer of 0-8; and m is 0 or 1.

Hereunder is provided a more detailed description of the present invention.

The present invention relates to a process of preparing thiomethylphenol derivatives, which comprises the steps of preparing a thiomethylphenol derivative by performing an reaction with a phenol derivative, a mercaptan derivative and paraformaldehyde in a solvent in the presence of both an heterocyclic amine base and acids, and purifying the obtained thiomethylphenol derivative using an acid, thereby enabling the manufacture of colorless thiomethylphenol derivatives having an improved discoloration with a higher conversion and purity under a relatively mild condition.

Conventionally, a phenol derivative is reacted a mercaptan derivative and paraformaldehyde in the presence of a basic amine, in particular a linear primary or secondary amine, to produce a thiomethylphenol derivative.

In an embodiment, the present invention relates to (i) a use of a certain heterocyclic amine that may minimize the steric hindrance against the reaction between two molecules comparing to the conventionally used linear secondary amine, along with (ii) a use of a polar solvent that may decrease the activation energy for the reaction between the base and the paraformaldehyde, thereby increasing the reaction rate.

In another embodiment, the present invention relates to aminomethanol, i.e. an intermediate product produced from a base and a paraformaldehyde, transforms into a highly reactive imine by the addition of an acid. This may maximize the reactivity with a phenol and maintain the reaction condition milder than that of the reaction between an aminomethanol and a phenol, and also prevent the oxidation of the base and finally inhibiting the discoloration.

Hereunder is provided a more detailed description of a process for preparing thiomethylphenol derivatives according to the present invention.

According to the present invention, a phenol derivative of Formula (II), a mercaptan derivative represented by $R^2SH$ and a paraformaldehyde are reacted in a solvent in the presence of both a $C_4$-$C_{10}$ heterocyclic amine base and an acid.

The phenol derivative of Formula (II), the mercaptan derivative and paraformaldehyde are widely used in the technical field to which the present invention pertains and are not limited to specific examples of compounds. Examples of the phenol derivative include without limitation o-cresol, p-cresol, 4-butylphenol and bisphenol. Examples of the mercaptan derivative include without limitation octane mercaptan, decane mercaptan, dodecane mercaptan, benzylmercaptan and thiophenol.

Raw reactants may be used in such a molar ratio that the thiomethylphenol derivatives of Formula (I) may be formed. In particular, paraformaldehyde may be used in the amount of 2-3 equivalents, preferably 2-2.5 equivalents relative to one equivalent of the phenol derivative. The mercaptan derivatives may be used in the amount of 2-3 equivalents, preferably 2-2.5 equivalents relative to one equivalent of the phenol derivative. If the amount of the paraformaldehyde is less than 2 equivalents, the reaction may not proceed sufficiently, which may in turn produce a mixture of monothiomethylphenol and dithiomethylphenol. If the amount is more than 3 equivalents, the time for the purification may be extended. Meanwhile, if the amount of the mercaptan derivatives is less than 2 equivalents, the reaction may not proceed sufficiently, which may in turn produce a mixture of monothiomethylphenol and dithiomethylphenol. If the amount is more than 3 equivalents, the generation of impurities increases and the time for purification may be prolonged.

The heterocyclic amine base is widely used in the technical field the present invention pertains to and is not limited to specific examples of compounds. Examples of the heterocyclic amine base include without limitation a $C_4$-$C_{10}$ heterocyclic amine, and in particular may be selected among piperidine, 2-methylpiperidine, pyrrolidine, 2-methylpyrrolidine, 2,6-dimethylpyrrolidine, piperazine, imidazole and a mixture thereof. The heterocyclic amine may be used in the amount of 0.05-0.5 equivalents, preferably 0.1-0.3 equivalents relative to one equivalent of the phenol derivatives. If the amount is less than 0.05 equivalents, the reaction time may be prolonged. If the amount is higher than 0.5 equivalents, the generation of impurities increased while the reaction time may be shortened.

The acid, which is used together with the heterocyclic amine base in the present invention, may be selected among an organic acid, an inorganic acid and a mixture thereof. Examples of the organic acid include without limitation (i) an aliphatic or aromatic organic acid having an functional group selected among a carboxylic acid, a sulfuric acid and a phosphoric acid; and (ii) an aliphatic or aromatic organic acid having both a functional group selected among alkyl, alkenyl, aryl, hydroxyl, thiol, amine, ether, ester, amide, ketone, aldehyde, ether, carboxyl, sulfone, phosphoryl groups and a combination thereof, and a functional group selected among a carboxylic acid, a sulfuric acid and a phosphoric acid.

The inorganic acid is widely used as a weak base in the technical field the present invention pertains to. Examples of the inorganic acid include carbonate, sulfate, and phosphorate of alkali metal or alkaline earth metal and a complex inorganic acid of heterogenous acid consisting of at least two oxyacids. Examples of the carbonate, sulfate and nitrate of alkali metal or alkaline earth metal include without limitation $XHCO_3$, $X_2CO_3$, $XHSO_4$, $X_2SO_4$, $XH_2PO_4$, $X_2HPO_4$ and $X_3PO_4$ where X is an alkali metal or an alkaline earth metal. Examples of the complex inorganic acid of heterogenous acid consisting of at least two oxyacids include without limitation clay and cation exchange resin.

The base may be used in the amount of 0.01-0.9 equivalents, preferably 0.4-0.8 equivalents relative to one equivalent of the base. The acid and the base may not work if the amount is less than 0.01 equivalents and higher than 0.9 equivalents, respectively.

Conventionally, the thiomethylphenol derivatives have been prepared at 120-150° C. for 3-6 hours depending on the kind of the base. In an embodiment of the present invention, the reaction for preparing the thiomethylphenol derivatives may be performed at a lowered temperature by 20-60° C. (i.e. at 90-150° C., preferably 90-120° C.) for a shortened period of time by more than 1-4 hours (i.e. for 0.5-3 hours, preferably 1-2 hours) by introducing both a heterocyclic amine and acids. If the reaction temperature is lower than 90° C., reaction may not proceed sufficiently. If the temperature is higher than 150° C., the economic efficiency may be lowered although the reaction may proceed well without causing the discoloration. Further, if the reaction time is shorter than 1 hour, the reaction may not proceed sufficiently. If the time is longer than 2 hours, the economic efficiency may be lowered although the discoloration may not happen.

The solvent may be selected from the group consisting of water, alcohol and a mixture thereof. Examples of the alcohol include without limitation $C_1$-$C_6$ low alcohol. The solvent may be used in the amount of 0.5-50 equivalents, preferably 1-20 equivalents relative to one equivalent of the base. Beyond the range, the reactivity may be deteriorated due to the lower reaction rate.

Meanwhile, another technical feature of the present invention lies in performing a purification using an acid to control the discoloration of thus prepared thiomethylphenol derivatives herein. Specifically, a remnant aminomethanol, which is produced as an intermediate during the manufacture of the thiomethylphenol derivatives, may be oxidized and cause the discoloration of the thiomethylphenol derivatives.

In an embodiment of the present invention, the product is purified using a given amount of an acid, which decomposes the aminomethanol or/and removes the aminomethanol through the neutralization, thus enabling to prepare colorless thiomethylphenol derivatives.

The acid described herein may also be used in performing the purification. The acid may be used for the purification in the amount of 1-50 equivalents, preferably 3-10 equivalents relative to one equivalent of the base. If the amount is less than one equivalent, the discoloration may happen. There may be no discoloration if the amount is higher than 50 equivalents.

The acid may be dissolved in a solvent or may be used in the form of a non-solution. When the acid is used in the solution form, the aforementioned solvent may also be used for dissolving the acid. Preferably, the solvent may be used in the amount of 0.1-10 equivalents relative to one equivalent of the acid.

The purified thiomethylphenol derivatives have a yellow index (YI) of 1-15, preferably 1-8.

EXAMPLES

The present invention is described more specifically by the following Examples. Examples herein are meant only to illustrate the present invention, but they should not be construed as limiting the scope of the claimed invention.

Example 1

Preparation of 2,4-bis(n-octylthiomethyl)-6-methylphenol

Acetic acid (0.2 equivalents) was added to the mixture of o-cresol (6.8 g), paraformaldehyde (4 g), n-octanethiol (18.5 g) and piperidine (0.2 equivalents) in water (2 equivalents), and the reaction was carried out at 120° C. for 2 hours. The resulting reaction solution was separated to obtain the organic layer, which was concentrated at a reduced pressure to give 2,4-bis(n-octylthiomethyl)-6-methylphenol. The conversion of thus obtained product was 100% and the purity was 97%.

Examples 2-8

Preparation of 2,4-bis(n-octylthiomethyl)-6-methylphenol

As described in Example 2-8 of Table 1, 2,4-bis(n-octylthiomethyl)-6-methylphenol was obtained by varying the bases, the acids, and the reaction conditions.

Comparative Examples 1-13

Preparation of 2,4-bis(n-octylthiomethyl)-6-methylphenol

As described in Comparative Examples 1-13 of Table 2, 2,4-bis(n-octylthiomethyl)-6-methylphenol was obtained in the absence of acids by varying the solvent, the bases, and the reaction conditions.

TABLE 2

| Comp. Ex. | Base | Solvent | Reaction condition (° C., hour) | Conversion (%) | Purity (%) |
|---|---|---|---|---|---|
| 1 | Piperidine | — | 150, 5 | 85 | 87 |
| 2 | Pyrrolidine | — | 150, 5 | 85 | 90 |
| 3 | Piperazine | — | 150, 5 | 80 | 83 |
| 4 | Dimethylamine | — | 120, 6 | 79 | 89 |
| 5 | Dipropylamine | — | 150, 5 | 0 | 0 |
| 6 | Dibutylamine | — | 150, 5 | 0 | 0 |
| 7 | Piperidine | Ethanol | 150, 5 | 95 | 93 |
| 8 | Piperidine | Water | 150, 4 | 98 | 95 |
| 9 | Pyrrolidine | Water | 150, 5 | 90 | 91 |
| 10 | Piperazine | Water | 150, 5 | 88 | 90 |
| 11 | Dimethylamine | Methanol | 120, 6 | 35 | 80 |
| 12 | Dipropylamine | Water | 150, 5 | 0 | 0 |
| 13 | Dibutylamine | Water | 150, 5 | 0 | 0 |

As shown in Tables 1 and 2, the reaction conditions were milder in Examples 1-8, where a base, an acid and a solvent were used, than those in Comparative Examples 1-6, where only a base was used, or than those in Comparative Examples 7-13, where a base and a solvent were used.

Specifically, Comparative Examples 4-6, where only conventional linear amines such as dimethylamine, dipropylamine and dibutylamine were used, showed no or relatively lower conversion of reaction, while Comparative Examples 1-3, where heterocyclic amines such as piperidine, pyrrolidine and piperazine were used as in the present invention, showed relatively higher conversion and resulted in highly pure liquid.

Further, Comparative Examples 11-13, where linear amines such as dimethylamine, dipropylamine and dibutylamine were used along with a solvent, showed no or relatively lower conversion, while Comparative Examples 7-10, where heterocyclic amines such as piperidine, pyrrolidine

TABLE 1

| Ex. | Base (equiv.) | Acid (equiv.) | Solvent (equiv.) | Reaction condition (° C., hour) | Conversion (%) | Purity (%) |
|---|---|---|---|---|---|---|
| 1 | Piperidine (0.2) | Acetic acid (0.2) | Water(2) | 120, 2 | 100 | 97 |
| 2 | Piperidine (0.2) | Phosphoric acid (0.2) | Water(2) | 120, 3 | 100 | 95 |
| 3 | Piperidine (0.2) | Propanic acid(0.1) Phosphoric acid(0.1) | Water(2) | 120, 2 | 100 | 96 |
| 4 | Piperidine (0.2) | Latic acid(0.1) Acetic acid(0.1) | Water(2) | 120, 2 | 100 | 99 |
| 5 | Piperidine (0.2) | Toluene sulfonic acid(0.2) | Water(2) | 120, 3 | 100 | 95 |
| 6 | Pyrrolidine (0.1) | Acetic acid (0.1) | Water(2) | 90, 2 | 100 | 97 |
| 7 | Piperazine (0.1) | Acetic acid (0.1) | Water(2) | 90, 2 | 95 | 96 |
| 8 | Pyrrolidine(0.1) Piperidine(0.1) | Acetic acid(0.1) Maleic acid(0.1) | Water(2) | 90, 2 | 100 | 98 | and piperazine were used along with a solvent, showed relatively higher conversion and resulted in highly pure liquid. Comparative Examples 11-13 and Comparative Examples 7-10 showed more severe conditions than those of Examples herein.

In conclusion, the combinational use of a heterocyclic amine, an acid and a solvent may enable the reaction herein to proceed at a relatively milder condition as disclosed in the present invention.

Example 9

Preparation of 2,6-bis n-octylthiomethyl)-4-tert-butylphenol

Acetic acid (0.2 equivalents) was added to the mixture of 4-tert-butylphenol (9.5 g), paraformaldehyde (4 g), n-octanethiol (18.5 g) and piperidine (0.2 equivalents), and the reaction was carried out at an appropriate reaction temperature for 1 hour. The resulting reaction solution was separated to obtain the organic layer, which was concentrated at a reduced pressure to give 2,6-bis(n-octylthiomethyl)-4-tert-butylphenol. The conversion of thus obtained product was 99% and the purity was 97%.

Example 10

Preparation of 2,2-bis[4,4'-dihydroxy-3,3'5,5'-tetrakis(n-octylthiomethyl)phenol]propane Acetic acid (0.2 equivalents) was added to the mixture of bisphenol (7.2 g), paraformaldehyde (4 g), n-octanethiol (18.5 g) and piperidine (0.2 equivalents), and the reaction was carried out at an appropriate reaction temperature for 1 hour. The resulting reaction solution was separated to obtain the organic layer, which was concentrated at a reduced pressure to give 2,2-bis[4,4'-dihydroxy-3,3'5,5'-tetrakis(n-octylthiomethyl)phenol]propane. The conversion of thus obtained product was 98% and the purity was 92%.

Example 11

Preparation of 2,4-bis(n-octylthiomethyl)-6-benzylphenol

Acetic acid (0.2 equivalents) was added to the mixture of 2-benzylphenol (11.6 g), paraformaldehyde (4 g), n-octanethiol (18.5 g) and piperidine (0.2 equivalents), and the reaction was carried out at an appropriate reaction temperature for 1 hour. The resulting reaction solution was separated to obtain the organic layer, which was concentrated at a reduced pressure to give 2,4-bis(n-octylthiomethyl)-6-benzylphenol. The conversion of thus obtained product was 95% and the purity was 90%.

Examples 12-16

The Purification of 2,4-bis(n-octylthiomethyl)-6-methylphenol

The organic layer was separated from the reaction products obtained in Example 1, washed with an acid or acids, and concentrated at a reduced pressure for 1 hour to give 2,4-bis (n-octylthiomethyl)-6-methylphenol as a colorless liquid. The transmittance of the concentrated product was measured at 425 nm using UV-VIS spectrometer, and the discoloration the concentrated product was determined by the yellowness index (YI).

Comparative Example 14

The Purification of 2,4-bis(n-octylthiomethyl)-6-methylphenol

The organic layer was separated from the reaction products obtained in Example 2 and concentrated at a reduced pressure for 1 hour to give 2,4-bis(n-octylthiomethyl)-6-methylphenol as a yellow liquid.

TABLE 3

| Examples | Acid (equiv.) | Transmittance (%) | YI |
| --- | --- | --- | --- |
| Com. Ex. 14 | — | 76-88 | 21.7 |
| Ex. 12 | $CaCO_3$ (1) | 95 | 4.6 |
| Ex. 13 | Phosphoric acid(2) | 94 | 5.1 |
| Ex. 14 | Toluene sulfonic acid(2) | 97 | 4.1 |
| Ex. 15 | Heteroacid(4) | 93 | 8.0 |
| Ex. 16 | Phosphoric acid(1) $CaCO_3(1)$ | 90 | 6.5 |

As shown in Table 3, the acid treatment followed by the concentration at a reduced pressure performed in Examples 12-16 provided colorless liquid products. In contrast, the concentration at a reduced pressure without the acid treatment performed in Comparative Example 14 produced yellow liquid products. The transmittance of the products obtained without the purification was remarkably lowered and their YI values were relatively high.

As described above, the present invention employs a combinational use of a heterocyclic amine, an acid and a solvent in preparing thiomethylphenol derivatives, thus showing an increased reaction rate and relatively higher yield and conversion in a relatively milder condition. Further, the discoloration of thiomethylphenol derivatives may also be improved by preventing the oxidation of a base through the purification using an acid. Therefore colorless thiomethylphenol derivatives obtained by the present invention may be applied to various fields.

What is claimed is:
1. A process of preparing a thiomethylphenol of Formula (I), which comprises a step of performing a reaction of a phenol derivative of Formula (II), a mercaptan derivative of $R^2SH$ and paraformaldehyde in a solvent in the presence of a $C_4$-$C_{10}$ heterocyclic amine base and acids:

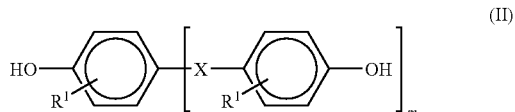

(II)

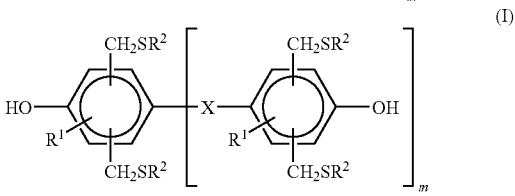

(I)

wherein $R^1$ is a hydrogen atom, a $C_1$-$C_{16}$ linear or branched alkyl, or an alkyl group comprising an aromatic group; $R^2$ is a $C_1$-$C_{16}$ linear or branched alkyl or an alkyl group comprising an aromatic group; X is —$(CH_2)_n$—, —$CMe_2$- or —Y— wherein Y is an aromatic compound selected from the group consisting of benzene, biphenyl, toluene and naphthalene or an aromatic compound having at least one substituted alkyl group; n is an integer of 0-8; and m is 0 or 1, and when m is 0, the phenyl ring is bonded to hydrogen.

2. The process of claim 1, wherein the $C_4$-$C_{10}$ heterocyclic amine base is selected from the group consisting of piperidine, 2-methylpiperidine, pyrrolidine, 2-methylpyrrolidine, 2,6-dimethylpyrrolidine, piperazine, imidazole and a mixture thereof.

3. The process of claim 1, wherein the acid is selected from the group consisting of an organic acid, an inorganic acid and a mixture thereof.

4. The process of claim 3, wherein the organic acid is an aliphatic or aromatic organic acid having a functional group selected from the group consisting of a carboxylic acid, a sulfuric acid and a phosphoric acid; or an aliphatic or aromatic organic acid having both a functional group selected from the group consisting of a carboxylic acid, a sulfuric acid and a phosphoric acid, and at least one substituted group selected from the group consisting of alkyl, alkenyl, aryl, hydroxyl, thiol, amine, ether, ester, amide, ketone, aldehyde, ether, carboxyl, sulfone and phosphoryl groups.

5. The process of claim 3, wherein the inorganic acid is (i) a carbonate, a sulfate or a phosphorate of an alkali metal or an alkaline earth metal selected from the group consisting of $XHCO_3$, $X_2CO_3$, $XHSO_4$, $X_2SO_4$, $XH_2PO_4$, $X_2HPO_4$ and $X_3PO_4$ or a complex inorganic acid of heterogeneous acid consisting of at least two oxyacids, wherein X is an alkali metal or an alkaline earth metal.

6. The process of claim 1, wherein the base is used in the amount of 0.05-0.5 equivalents relative to one equivalent of the phenol derivative.

7. The process of claim 1, wherein the acid is used in the amount of 0.01-0.9 equivalents relative to one equivalent of the base.

8. The process of claim 1, wherein the solvent is water or alcohol.

9. The process of claim 1, wherein the solvent is used in the amount of 0.5-50 equivalents relative to one equivalent of the base.

10. The process of claim 1, wherein the reaction is carried out at 90-150° C.

11. The process of claim 1, wherein the thiomethylphenol produced thereof is further purified by acids.

12. The process of claim 11, wherein the amount of the acid used during the purification is 1-50 equivalents relative to one equivalent of the base used during the reaction.

13. The process of claim 11, wherein the purified thiomethylphenol has a yellow index (YI) of 1-15.

14. The process of claim 2, wherein the base is used in the amount of 0.05-0.5 equivalents relative to one equivalent of the phenol derivative.

15. The process of claim 8, wherein the solvent is used in the amount of 0.5-50 equivalents relative to one equivalent of the base.

16. The process of claim 12, wherein the purified thiomethylphenol has a yellow index (YI) of 1-15.

* * * * *